United States Patent [19]

Tsutsumi et al.

[11] 4,152,421

[45] May 1, 1979

[54] DENTIFRICE COMPOSITION

[75] Inventors: Hisao Tsutsumi, Sakura; Toshiro Asakawa, Funabashi; Shizuo Hayashi, Saitama, all of Japan

[73] Assignee: Kao Soap Co., Ltd., Tokyo, Japan

[21] Appl. No.: 838,559

[22] Filed: Sep. 30, 1977

[30] Foreign Application Priority Data

Oct. 12, 1976 [JP] Japan ................................ 51-122178

[51] Int. Cl.$^2$ ................................................ A61K 7/16
[52] U.S. Cl. ...................................... 424/57; 260/963; 260/924; 260/925; 260/956
[58] Field of Search ................... 424/57; 260/963, 924, 260/925, 956

[56] References Cited

U.S. PATENT DOCUMENTS 4,036,950  7/1977  Baines et al. ........................... 424/57

*Primary Examiner*—Natalie Trousof
*Assistant Examiner*—Robert C. Whittenbaugh
*Attorney, Agent, or Firm*—Blanchard, Flynn, Thiel, Boutell & Tanis

[57] ABSTRACT

A dentifrice composition containing as the active foaming agent (I) a monoalkyl phosphate ester salt and (II) a dialkyl phosphate ester salt, wherein said alkyls have 10 to 14 carbon atoms and the weight ratio of I:II is from 100:0 to 70:30.

6 Claims, No Drawings

DENTIFRICE COMPOSITION

BACKGROUND OF THE INVENTION

1. Field of the Invention

The present invention relates to a dentifrice composition comprising an alkyl phosphate ester salt as a foaming agent, which foaming agent does not affect the tastes or flavors of foods and drinks.

2. Description of the Prior Art

In general, dentifrices are used at the time of rising from sleep, after eating and before sleeping to remove residues from the interior of the mouth, to keep the interior of the mouth clean and to obtain a refreshing feeling in the mouth. Because dentifrices are applied to the interior of the mouth and they are often used before and after eating, the tastes of foods and drinks are often affected by dentifrices.

More specifically, some kinds of dentifrices have effects on the tastes or flavors of foods and drinks and change them to bitter or astringent tastes or flavors.

In general, dentifrice compositions are formed by mixing a foaming agent with a polishing agent, binders, a humectant, a medicinal ingredient, a sweetening agent, a flavor and water. Among these components of the dentifrice composition, the component that changes the tastes of foods and drinks is the surface active agent that is ordinarily used as the foaming agent. It is known that the other components have no substantial effects on the tastes of foods and drinks.

Various sulfate ester salts and sulfonic acid salts such as alkyl sulfate ester salts, α-olefin-sulfonic acid salts and monoglyceride sulfate ester salts have heretofore been widely used as foaming agents for dentifrice compositions because of their good foaming property. Each of these sulfate ester salts and sulfonic acid salts has an inherent bitter taste, more or less. Accordingly, when a dentifrice composition containing such surface active agent is used, a bitter taste remains in the mouth because of the residual surface active agent left in the oral cavity and the taste of food or drink taken afterwards is changed by the aftertaste of the residual surface active agent. This undesirable phenomenon is especially conspicuous in the case of citrus fruits, such as lemons and oranges, and foods and drinks having a low pH such as lactic acid beverages.

It is known that among the surface active agents, carboxylic acid salts, phosphate ester salts and nonionic surface active agents have no substantial after effects on the tastes and flavors of foods and drinks, but these surface active agents per se have an undesirable taste and their forming property is extremely low when they are incorporated in a dentifrice composition. Therefore, they have scarcely been used in dentifrice compositions.

SUMMARY OF THE INVENTION

We have discovered a dentifrice composition having a good forming property and which does not change the tastes of foods and drinks, which composition contains as a foaming agent specific alkyl phosphate esters having the formulae given below. Based on this discovery, we have now completed the present invention.

More specifically, in accordance with the present invention, there is provided a dentifrice composition comprising, as a foaming component, a monoalkyl phosphate ester salt having the formula (I):

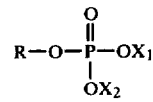

wherein R is alkyl or alkenyl having 10 to 14 carbon atoms, $X_1$ is alkali metal or alkanolamine, and $X_2$ is hydrogen, alkali metal or alkanolamine,
and a dialkyl phosphate ester salt having the formula (II):

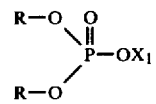

wherein R and $X_1$ are the same as defined above,
wherein the mixing weight ratio of the monoalkyl phosphate ester salt of formula (I) to the dialkyl phosphate ester salt of formula (II) is in the range of from 100:0 to 70:30.

The sum of the amounts of the alkyl phosphate ester salts of formulae (I) and (II), employed as the foaming agent, is from 0.2 to 5.0% by weight, preferably 1.0 to 4.0% by weight, based on the total weight of the dentifrice composition.

The alkyl phosphate ester salts that are used in the present invention can be obtained, for example, by hydrolyzing a mono-long-chain-alkyl phosphorodichloridate obtained by reacting a long-chain aliphatic alcohol with phosphorus oxychloride. Each of the known surface active agents of the phosphate ester type is a sesquiphosphate and is composed of a mixture of equal amounts of a monoester and a diester, or a mixture including a monoester, a diester and a triester. Accordingly, these surface active agents are extremely poor in water solubility and foaming property and they are not suitable as foaming agents for dentifrice compositions. It is known to adduct ethylene oxide units to such phosphate ester-type surface active agents, but because this modified agent has no substantial foaming property when it is incorporated into a dentifrice composition and it has a very bad taste, it is not suitable as a foaming agent in a dentifrice composition.

The dentifrice composition of the present invention comprises as a foaming component an alkyl phosphate ester salt containing at least 70% by weight of a monoalkyl phosphate ester of the above formula (I) having an excellent foaming property. In order to attain the intended effect of the present invention, it is preferred that the carbon number of the group R is in the range of from 12 to 14. However, if $X_1$ and $X_2$ are appropriately chosen, R having a carbon atom number of 10 to 12 can be used.

In addition to the alkyl phosphate ester employed as the foaming component, the dentifrice composition of the present invention comprises components customarily used in this field, such as a polishing agent (abrasive agent), a binder, a humectant, a medicinal agent, a sweetening agent, a flavor and water. As the polishing agent, there can be mentioned calcium hydrogenphosphate, calcium carbonate, alumina, calcium pyrophosphate and the like. As the binder, there can be mentioned, for example, sodium carboxymethylcellulose, hydroxyethylcellulose, carrageenan, sodium alginate, hippunea, gum arabic, xanthane gum, locust bean gum, montmorillonite and hectorite. As the humectant, there can be used, for example, glycerin, sorbitol and propylene glycol. As the sweetening agent, there can be used, for example, soluble saccharin. As the medicinal agent, there can be mentioned, for example, an antiseptic, an antiphlogistic agent and a fungicide. In the case of a dental cream, a typical composition comprises 0.3 to 5.0% by weight of a binder, 5 to 40% by weight of a humectant, 0.2 to 5% by weight of a foaming agent and 5 to 70% by weight of a polishing agent, with the balance being water.

The present invention will now be described in detail by reference to the following illustrative experiments and examples, in which all references to "%" mean % by weight.

EXPERIMENT 1

The foaming properties of 0.5% aqueous solutions of surface active agents having the compositions indicated below were tested. In the foaming test, 0.1% of hydrous lanolin was added as an artificial soil to an aqueous solution of a sample surface active agent, and the solution was charged in a cylinder and agitated for 5 minutes at 25° C. and 1000 rpm by using a horizontal propeller while reversing the rotation direction at intervals of 30 seconds. The foaming property was evaluated based on the volume of the foam measured after 30 seconds had passed from completion of the agitation. The results obtained are shown in Table 1. For comparison, an ethylene oxide adduct of phosphate ester salt, namely sodium polyoxyethylene lauryl phosphate, was similarly tested and its foaming property was evaluated.

The compositions of the surface active agents tested are as follows:

| Sample | Formula Compound (I) /Formula Compound (II) Weight Ratio |
|---|---|
| a | 100 : 0 |
| b | 90 : 10 |
| c | 80 : 20 |
| d | 70 : 30 |
| e | 60 : 40 |
| f | 50 : 50 |
| g | 40 : 60 |
| h | 30 : 70 |
| i | 20 : 80 |
| j | 10 : 90 |
| k | 0 : 100 |

Compound (I):

$$R-O-\overset{\overset{O}{\|}}{\underset{OX_2}{P}}-OX_1$$

Compound (II):

$$R-O-\overset{\overset{O}{\|}}{\underset{\underset{R}{O}}{P}}-OX_1$$

Table 1
Results of Foaming Test

| R in Compound (I) | $C_{10}H_{21}$ | $C_{12}H_{25}$ | $C_{14}H_{29}$ | $C_{16}H_{33}$* | $C_{12}H_{25}O(EO)_3-\overset{\overset{O}{\|}}{\underset{OH}{P}}-ONa$* |
|---|---|---|---|---|---|
| $X_2, X_1$ in Compound (I) | H,Na | H,Na | Na,Na | H,Na | |
| R in Compound (II) | $C_{10}H_{21}$ | $C_{12}H_{25}$ | $C_{14}H_{29}$ | $C_{16}H_{33}$ | $C_{12}H_{25}O(EO)_3-\overset{\overset{O}{\|}}{\underset{\underset{C_{12}H_{25}}{\underset{O}{(EO)}}}{P}}-ONa$ |
| $X_1$ in Compound (II) | Na | Na | Na | Na | |
| (I)/(II) Weight Ratio | | | Volume (ml) of foam | | |
| a | 185 | 204 | 226 | 62 | 3 |
| b | 164 | 202 | 218 | 17 | — |
| c | 146 | 202 | 201 | 0 | — |
| d | 125 | 197 | 185 | 0 | — |
| *e | 48 | 32 | 24 | 0 | — |
| *f | 25 | 5 | 0 | 0 | 0 |
| *g | 3 | 0 | 0 | 0 | — |
| *h | 0 | 0 | 0 | 0 | — |
| *i | 0 | 0 | 0 | 0 | — |
| *j | 0 | 0 | 0 | 0 | — |
| *k | 0 | 0 | 0 | 0 | 0 |

Note
*comparison.
—: no data

As will be apparent from the results shown in Table 1, foaming agents (a to d) in which the weight ratio of the formula (I) compound and the formula (II) compound is in the range of from 100:0 to 70:30 have a good foaming property, and they are suitable for attaining the object of the present invention. When the content of the formula (I) compound is lower than 70%, the foaming property is drastically degraded and the intended purposes of the present invention cannot be attained. Accordingly, such low contents of the formula (I) compound are not included in the scope of the present invention. For similar reasons, the carbon atom number of R must be in the range of 10 to 14 so as to obtain good results. R having a carbon atom number outside this range is not included in the scope of the present invention.

The ethylene oxide-adduct comparative agent has no substantial foaming property and it is not suitable as a foaming agent for a dentifrice composition, and it is not included in the scope of the present invention.

EXPERIMENT 2

1% Aqueous solutions of foaming agents of the present invention and comparative foaming agents for dentifrice compositions were subjected to a mouth rinsing test conducted by a panel of 5 experts. The taste of such solution during rinsing and after rinsing was organoleptically evaluated according to the following rating criteria:

During Rinsing

O: no substantial taste
Δ: slightly bitter or astringent
X: strongly bitter or astringent
XX: very strongly bitter or astringent After Rinsing O: no substantial aftertaste
Δ: slightly bitter aftertaste
X: strongly bitter aftertaste
XX: very strongly bitter aftertaste
The results obtained are shown in Table 2.

determined whether or not the taste of the drink was changed. The results obtained are shown in Table 3.

| Recipe (%) of Dental Cream | |
|---|---|
| Dicalcium phosphate dihydrate | 45.0 |
| Sodium carboxymethylcellulose | 1.3 |
| Glycerin | 20.0 |
| Sodium saccharin | 0.1 |
| Sodium benzoate | 0.2 |
| Methyl p-hydroxybenzoate | 0.1 |
| Flavor | 0.9 |
| Pure water | 30.4 |
| Sample foaming agent | 2.0 |
| Total | 100.0 |

The evaluation was made according to the following rating criteria:
O: taste of drink hardly changed
Δ: taste of drink slightly changed
X: taste of drink considerably changed
XX: taste of drink completely changed and lost Table 3

| | Change of Tastes of Drinks | | | | | | | | | |
|---|---|---|---|---|---|---|---|---|---|---|
| Sample Foaming Agent | Japanese Tea | | | Orange Juice | | | Lactic Acid Beverage | | |
| Present Invention | Δ | X | XX | Δ | X | XX | Δ | X | XX |
| monopotassium monodecyl phosphate | 5 | 2 | 0 | 0 | 4 | 3 | 0 | 0 | 5 | 2 | 0 | 0 |
| monosodium monolauryl phosphate | 7 | 0 | 0 | 0 | 5 | 2 | 0 | 0 | 6 | 1 | 0 | 0 |
| disodium monomyristyl phosphate | 6 | 1 | 0 | 0 | 6 | 1 | 0 | 0 | 6 | 1 | 0 | 0 |
| mono(triethanolamine) monomyristyl phosphate | 2 | 3 | 2 | 0 | 4 | 3 | 0 | 0 | 4 | 3 | 0 | 0 |
| Comparison | | | | | | | | | | | | |
| sodium lauryl sulfate | 0 | 2 | 2 | 3 | 0 | 0 | 0 | 7 | 0 | 0 | 6 | 1 |
| sodium α-olefin-sulfonate | 0 | 2 | 3 | 2 | 0 | 0 | 0 | 7 | 0 | 0 | 2 | 5 |
| potassium laurate | 0 | 3 | 4 | 0 | 0 | 0 | 6 | 1 | 0 | 0 | 5 | 2 |
| sodium salts of monoglyceride sulfate ester | 0 | 4 | 3 | 0 | 0 | 0 | 6 | 1 | 0 | 1 | 5 | 1 |
| sodium dodecyl benzene-sulfonate | 0 | 2 | 2 | 3 | 0 | 0 | 0 | 7 | 0 | 0 | 6 | 1 |

Table 2

| Taste of Aqueous Solution of Surface Active Agent | | |
|---|---|---|
| Sample | During | After |
| Present Invention | Rinsing | Rinsing |
| monopotassium monodecyl phosphate | | |
| monosodium monolauryl phosphate | | |
| disodium monomyristyl phosphate | | |
| mono(triethanolamine) monomyristyl phosphate | Δ | |
| 90% of monosodium monolauryl phosphate plus 10% of sodium dilauryl phosphate | | |
| Comparison | | |
| sodium lauryl sulfate | X | XX |
| sodium α-olefin-sulfonate | X | XX |
| potassium laurate | XX | X |
| sodium salts of monoglyceride sulfate ester | Δ | Δ |
| sodium dodecyl benzene-sulfonate | XX | XX |
| disodium mono-oleyl phosphate | X | Δ |
| sodium sesqui-lauryl phosphate | Δ | Δ |

From the results shown in Table 2, it will readily be understood that the foaming agents of the present invention are superior to conventional dentifrice foaming agents with respect to the residual taste of the surface active agent per se either during mouth rinsing or after mouth rinsing.

EXPERIMENT 3

Dental creams including a foaming agent of the present invention or a comparative foaming agent were prepared according to the recipe indicated below. A panel of 21 men cleaned their teeth for 3 minutes by using about 2 g of a sample dental cream, and immediately after completion of the cleaning operation, Japanese tea, orange juice or lactic acid beverage was given to the men of the panel and it was organoleptically As will be apparent from the results shown in Table 3, when a dentifrice containing the foaming agent of the present invention is used, the tastes of foods and drinks are scarcely changed, whereas the tastes of foods and drinks are changed in the case of conventional foaming agents.

As will readily be understood from the results of Experiments 1 to 3, when a conventional surface active agent for a dentifrice is used as a foaming agent, it is very difficult to obtain a dentifrice having a good foaming property and which also does not change the tastes of foods and drinks, but when the compound of the present invention is used, a dentifrice having an excellent foaming property and which does not change the tastes of foods and drinks can be obtained very easily.

Examples of the dentifrice composition of the present invention will now be described.

Example 1 (Dental Cream)

| Carrageenan | 1.4% |
|---|---|
| Glycerin | 20.0% |
| Sodium saccharin | 0.12% |
| Dicalcium phosphate dihydrate | 49.0% |
| Disodium monomyristyl phosphate | 1.8% |
| Sodium dimyristyl phosphate | 0.2% |
| Sodium monofluorophosphate | 0.7% |
| Flavor | 0.9% |
| Sodium benzoate | 0.2% |
| Pure water | balance |
| Total | 100.0% |

Sodium saccharin, sodium benzoate, glycerin and carrageenan were added to pure water and the mixture was heated at 40° to 60° C. to form a solution. Then, dicalcium phosphate dihydrate and sodium monofluorophosphate were added to the solution and the mixture was agitated. Further, a mixture of disodium monomyristyl phosphate and sodium dimyristyl phosphate was added to the mixture. Then, the resulting mixture was degasified and agitated, and the flavor was added thereto. The mixture was further degasified and agitated to form a dental cream composition.

In the following Examples, dentifrices having the compositions indicated below were prepared according to methods similar to the method described in Example 1.

Example 2 (Dental Cream)

| | |
|---|---|
| Sodium carboxymethylcellulose | 1.25% |
| Propylene glycol | 4.0% |
| Sorbitol | 20.0% |
| Monosodium monolauryl phosphate | 2.0% |
| Sodium dilauryl phosphate | 0.2% |
| Sodium saccharin | 0.10% |
| Sodium benzoate | 0.30% |
| Flavor carbonate | 45.0% |
| Flavor | 0.8% |
| Pure water | balance |
| Total | 100.0% |

Example 3 (Dental Cream)

| | |
|---|---|
| Carrageenan | 1.3% |
| Propylene glycol | 3.0% |
| Sorbitol | 20.0% |
| Monotriethanolamine monomyristyl phosphate | 2.0 |
| Sodium saccharin | 0.10% |
| Methyl p-hydroxybenzoate | 0.20% |
| Insoluble sodium metaphosphate | 49.0% |
| Flavor | 0.8% |
| Pure water | balance |
| Total | 100.0% |

Example 4 (Dental Cream)

| | |
|---|---|
| Carrageenan | 1.2% |
| Sorbitol | 18.0% |
| Propylene glycol | 3.0% |
| Monopotassium monodecyl phosphate | 2.0% |
| Sodium saccharin | 0.14% |
| Methyl p-hydroxybenzoate | 0.20% |
| Calcium pyrophosphate | 48.0% |
| Flavor | 0.9% |
| Disodium phosphate | 2.5% |
| Pure water | balance |
| Total | 100.0% |

Example 5 (Wet Toothpaste)

| | |
|---|---|
| Heavy calcium carbonate | 40.0% |
| Light calcium carbonate | 35.0% |
| Glycerin | 12.0% |
| Sodium saccharin | 0.15% |
| Disodium monolauryl phosphate | 1.5% |
| Flavor | 0.9% |
| Pure water | balance |
| Total | 100.0% |

Example 6 (Tooth Powder)

| | |
|---|---|
| Light calcium carbonate | 55.0% |
| Heavy calcium carbonate | 40.0% |
| Sodium saccharin | 0.2% |
| Monosodium monomyristyl phosphate | 1.5% |
| Sodium dimyristyl phosphate | 0.2% |
| Flavor | 0.9% |
| Pure water | balance |
| Total | 100.0% |

The embodiments of the invention in which an exclusive property or privilege is claimed are defined as follows:

1. A dentifrice composition in which the active foaming component consists essentially of a monoalkyl phosphate ester salt having the formula (I):

wherein R is alkyl or alkenyl having 10 to 14 carbon atoms, $X_1$ is alkali metal or alkanolamine, and $X_2$ is hydrogen, alkali metal or alkanolamine, and a dialkyl phosphate ester salt having the formula (II):

wherein R and $X_1$ are the same as defined above, the mixing weight ratio of said monoalkyl phosphate ester salt (I) to said dialkyl phosphate ester salt (II) being in the range of from 100:0 to 70:30.

2. A dentifrice composition as set forth in claim 1 wherein the sum of the amounts of said alkyl phosphate esters of formula (I) and formula (II) is from 0.2 to 5.0% by weight, based on the total weight of said dentifrice composition, the balance of said dentifrice composition consisting essentially of conventional dentifrice ingredients.

3. A dentifrice composition as set forth in claim 1 wherein the mixing weight ratio of said monoalkyl phosphate ester salt of formula (I) to the dialkyl phosphate ester salt of formula (II) is in the range of from 100:0 to 85:15.

4. A dentifrice composition as set forth in claim 1 wherein in said monoalkyl phosphate ester of formula (I), $X_1$ is sodium or potassium and $X_2$ is hydrogen.

5. A dentifrice composition as claimed in claim 1 wherein R contains 12 to 14 carbon atoms.

6. A dentifrice composition as claimed in claim 1 wherein the sum of the amounts of said formula (I) compound and said formula (II) compound is from one to 4 percent by weight, and the balance of said composition consists essentially of from 0.3 to 5 percent by weight of a dentally acceptable binder, from 5 to 40 percent by weight of a dentally acceptable humectant and from 5 to 70 percent by weight of a dentally acceptable polishing agent.

* * * * *